(12) United States Patent
Morimoto et al.

(10) Patent No.: US 11,696,737 B2
(45) Date of Patent: Jul. 11, 2023

(54) ULTRASONIC ENDOSCOPE INCLUDING TREATMENT-TOOL ERECTING BASE FOR ERECTING TREATMENT TOOL THAT IS LED OUT FROM OPENING FORMED IN DISTAL END RIGID PORTION OF ENDOSCOPE INSERTION SECTION

(71) Applicant: FUJIFILM Corporation, Tokyo (JP)

(72) Inventors: Yasuhiko Morimoto, Ashigarakami-gun (JP); Toshizumi Tanaka, Ashigarakami-gun (JP); Shozo Iyama, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 874 days.

(21) Appl. No.: 16/577,894

(22) Filed: Sep. 20, 2019

(65) Prior Publication Data

US 2020/0015782 A1   Jan. 16, 2020

Related U.S. Application Data

(63) Continuation of application No. PCT/JP2018/003868, filed on Feb. 5, 2018.

(30) Foreign Application Priority Data

Mar. 31, 2017   (JP) .............................. JP2017-071147

(51) Int. Cl.
*A61B 1/00* (2006.01)
*A61B 1/018* (2006.01)
(Continued)

(52) U.S. Cl.
CPC ........ *A61B 8/0841* (2013.01); *A61B 1/00087* (2013.01); *A61B 1/015* (2013.01);
(Continued)

(58) Field of Classification Search
None
See application file for complete search history.

(56) References Cited

U.S. PATENT DOCUMENTS

2005/0222493 A1   10/2005   Kohno
2006/0184035 A1*  8/2006   Kimura ................ A61B 8/4488
                                                    600/466
(Continued)

FOREIGN PATENT DOCUMENTS

CN   102283624 A   12/2011
CN   105596028 A    5/2016
(Continued)

OTHER PUBLICATIONS

Chinese Office Action and Search Report for corresponding Chinese Application No. 201880022392.8, dated Aug. 17, 2021, with an English translation.

(Continued)

*Primary Examiner* — John P Leubecker
(74) *Attorney, Agent, or Firm* — Birch, Stewart, Kolasch & Birch, LLP

(57) ABSTRACT

An ultrasonic endoscope includes a distal end rigid portion that is located at a distal end of an insertion section; a treatment tool lead-out portion that is disposed on a proximal end side of an ultrasonic transducer and that includes an erecting base housing portion that has an opening whose opening direction is toward one side in a first direction, an opening forming surface in which the opening is formed, and a treatment-tool erecting base that is disposed in an inside of the erecting base housing portion and that changes a lead-out direction of a treatment tool; and an observation window that is disposed in an observation means forming surface located on the proximal end side of the opening forming surface. The position of the observation window in (Continued)

the first direction is located on one side in the first direction relative to a one-side opening position of the opening.

17 Claims, 13 Drawing Sheets

(51) Int. Cl.
   *A61B 1/12* (2006.01)
   *A61B 8/08* (2006.01)
   *A61B 1/015* (2006.01)
   *A61B 8/12* (2006.01)
   *A61B 8/00* (2006.01)
   *A61B 1/06* (2006.01)

(52) U.S. Cl.
   CPC ............... *A61B 1/018* (2013.01); *A61B 1/06* (2013.01); *A61B 1/126* (2013.01); *A61B 8/12* (2013.01); *A61B 8/445* (2013.01)

(56) References Cited

U.S. PATENT DOCUMENTS

| | | | | |
|---|---|---|---|---|
| 2007/0249940 | A1* | 10/2007 | Kohno | A61B 8/445 600/463 |
| 2011/0301413 | A1* | 12/2011 | Morimoto | A61B 1/00087 600/104 |
| 2016/0073860 | A1 | 3/2016 | Morimoto | |
| 2016/0089004 | A1 | 3/2016 | Morimoto | |
| 2016/0089124 | A1 | 3/2016 | Morimoto et al. | |
| 2016/0278809 | A1* | 9/2016 | Sato | A61B 8/12 |

FOREIGN PATENT DOCUMENTS

| | | |
|---|---|---|
| EP | 2 671 514 A1 | 12/2013 |
| JP | H09108224 A * | 4/1997 |
| JP | 2005-287593 A | 10/2005 |
| JP | 2007-252457 A | 10/2007 |
| JP | 2011-206428 A | 10/2011 |
| JP | 2017-23480 A | 2/2017 |

OTHER PUBLICATIONS

Japanese Notice of Reasons for Refusal for corresponding Japanese Application No. 2020-177255, dated Oct. 4, 2021, with an English translation.
Chinese Office Action tor corresponding Chinese Application No. 201880022392.8, daled Feb. 23, 2022, with English translation.
Chinese Office Action and Search Report for corresponding Chinese Application no. 201880022392.8, dated Nov. 4, 2021, with an English translation.
Japanese Decision of Refusal for corresponding Japanese Application No. 2020-177255, dated Feb. 22, 2022, with an English translation.
Extended European Search Report dated Feb. 25, 2020, for corresponding European Application No. 18775274.6.
International Preliminary Report on Patentability and English translation of the Written Opinion of the International Searching Authority (Forms PCT/IB/326, PCT/IB/373, and PCT/ISA/237) for International Application No. PCT/JP2018/003868, dated Oct. 10, 2019.
International Search Report (Form PCT/ISA/210) for International Application No. PCT/JP2018/003868, dated May 1, 2018, with English translation.
Japanese Office Action dated Apr. 7, 2020, for corresponding Japanese Application No. 2019-508680, with an English translation.
Japanese Office Action dated Jul. 27, 2020 for corresponding Application No. 2019-508680, along with an English translation.
European Communication pursuant to Article 94(3) EPC for European Application No. 18775274.6, dated May 11, 2022.

* cited by examiner

ULTRASONIC ENDOSCOPE INCLUDING TREATMENT-TOOL ERECTING BASE FOR ERECTING TREATMENT TOOL THAT IS LED OUT FROM OPENING FORMED IN DISTAL END RIGID PORTION OF ENDOSCOPE INSERTION SECTION

CROSS-REFERENCE TO RELATED APPLICATIONS

This application is a Continuation of PCT International Application No. PCT/JP2018/003868 filed on Feb. 5, 2018, which claims priority under 35 U.S.C § 119(a) to Japanese Patent Application No. 2017-071147 filed on Mar. 31, 2017. Each of the above application(s) is hereby expressly incorporated by reference, in its entirety, into the present application.

BACKGROUND OF THE INVENTION

1. Field of the Invention

The present invention relates to an ultrasonic endoscope, and, in particular to an ultrasonic endoscope including a treatment-tool erecting base for erecting a treatment tool that is led out from an opening formed in a distal end rigid portion of an endoscope insertion section.

2. Description of the Related Art

Some existing ultrasonic endoscopes known to date include an erecting base in a distal end part of an insertion section that is inserted into a body cavity. Such an ultrasonic endoscope can erect a treatment tool, which is inserted into a treatment tool insertion channel and led out from a treatment tool lead-out portion at the distal end part, and can also adjust the lead-out direction of the treatment tool by changing the erection angle of the erecting base.

For example, JP2005-287593A describes an endoscope configured as follows: a treatment tool lead-out portion has an erecting base, an erecting lever is coupled to the erecting base via a rotation shaft, an operation wire is coupled to the erecting lever, and the operation wire can be pushed or pulled by operating an operation unit that is disposed continuously with a proximal end portion of an insertion section.

SUMMARY OF THE INVENTION

However, in the ultrasonic endoscope described in JP2005-287593A, which includes the erecting base, an observation portion is disposed on a side of the treatment-tool erecting base (treatment tool lead-out portion). Therefore, when the treatment tool is led out, the treatment tool enters the field of view from the periphery of a monitor screen. Accordingly, the ultrasonic endoscope has low accuracy in positioning the treatment tool to a portion where a puncture needle or a stent is to be inserted. Moreover, when placing a stent, a proximal end portion (proximal side) of the stent needs to be exposed from a tissue. However, because it is difficult to observe an insertion point in the optical field of view in a state in which an ultrasonic transducer is made to be in contact with a surface of the tissue, it is necessary to change the field of view by pulling the insertion section in order to perform observation.

The present invention has been made under such circumstances, and an object of the present invention is to provide an ultrasonic endoscope that can observe even a proximal end portion side of a treatment tool in the field of view of an observation window.

To achieve the object, the present invention provides an ultrasonic endoscope including: a distal end rigid portion that is located at a distal end of an endoscope insertion section; an ultrasonic transducer that is disposed in the distal end rigid portion; a treatment tool lead-out portion that is disposed on a proximal end side of the ultrasonic transducer and that comprises an erecting base housing portion that has an opening whose opening direction is toward one side in a first direction that is perpendicular to an axial direction of the distal end rigid portion or whose opening direction is a direction that has a component toward the one side in the first direction and a component toward a distal end side in the axial direction of the distal end rigid portion, an opening forming surface in which the opening is formed and that has a normal component in the opening direction, a treatment tool lead-out port that communicates with an inside of the erecting base housing portion and from which a treatment tool is led out, and a treatment-tool erecting base that is disposed in the inside of the erecting base housing portion and that changes a lead-out direction of the treatment tool led out from the treatment tool lead-out port; and an observation window that is disposed on a proximal end side of the opening forming surface and that is disposed in an observation means forming surface that has a normal component toward the distal end side in the axial direction of the distal end rigid portion. When a position of an end portion of the opening that is furthest toward the one side in the first direction is defined as a one-side opening position, a position of the observation window in the first direction is located on the one side in the first direction relative to the one-side opening position.

If the opening is located on the proximal end side of the observation window as in existing ultrasonic endoscopes, only a part of a treatment tool on the distal end side relative to the observation window is within the field of view of the observation window, and it is not possible to check through the observation window depending on a treatment target position to be treated with the treatment tool. In the present invention, the opening for leading out a treatment tool is disposed on the distal end side relative to the observation window. Moreover, the position of the observation window in the first direction is located on the one side in the first direction relative to the one-side opening position of the opening. Thus, a blind area where a treatment tool led out from the opening is not within the field of view of the observation window can be reduced. Accordingly, treatment can be performed while checking through the observation window, and treatment can be reliably performed at a target position.

According to another aspect of the present invention, preferably, the ultrasonic transducer has an ultrasound transmitting/receiving surface that is formed in a curved shape in the axial direction of the distal end rigid portion.

The present invention can be appropriately used for a convex-type ultrasonic endoscope in which the ultrasound transmitting/receiving surface of the ultrasonic transducer is formed in a curved shape in the axial direction of the distal end rigid portion.

According to another aspect of the present invention, preferably, the ultrasound transmitting/receiving surface has a vertex that is located at an end portion thereof that is furthest toward the one side in the first direction; and, when a position of the vertex in the first direction is defined as a vertex position and a position of an end portion of the opening that is furthest toward the other side in the first direction is defined as an other-side opening position, the vertex position is identical to the other-side opening position or is located on the one side in the first direction relative to the other-side opening position.

This aspect defines the positions of the opening and the ultrasonic transducer. By locating the vertex position of the ultrasound transmitting/receiving surface in the first direction to be identical to the other-side opening position or on the one side in the first direction relative to the other-side opening position, a treatment tool led out from the opening can be made to be closer to the ultrasonic transducer. By making also the treatment tool be closer to the ultrasonic transducer, a position observed by the ultrasonic observation position can be treated with a treatment tool.

According to another aspect of the present invention, preferably, when a position of the treatment tool lead-out port in the first direction is defined as a lead-out port position, the vertex position is identical to the lead-out port position or is located on the one side in the first direction relative to the lead-out port position.

This aspect defines the positions of the treatment tool lead-out port and the ultrasonic transducer. A treatment tool passes through a treatment tool insertion channel formed in the endoscope insertion section and is led out from the opening formed on one side in the first direction. Accordingly, by locating the vertex position of the ultrasound transmitting/receiving surface in the first direction to be identical to the lead-out port position or on the one side in the first direction relative to the lead-out port position, a treatment tool can be guided to the vicinity of the ultrasonic transducer. Thus, treatment with a treatment tool can be performed at a position observed by ultrasonic observation.

According to another aspect of the present invention, preferably, the ultrasonic endoscope has a standing wall portion around the opening, the standing wall portion standing from the opening; and, when a position of an end portion of an upper edge of the standing wall portion that is furthest toward the one side in the first direction is defined as a one-side wall upper end position, the position of the observation window in the first direction is located on the one side in the first direction relative to the one-side wall upper end position.

With this aspect, because the standing wall portion is provided around the opening, horizontal displacement of a treatment tool led out from the opening can be prevented, and treatment with the treatment tool can be reliably performed at a target position. Moreover, because the position of the observation window is on the one side in the first direction relative to the one-side wall upper end position, treatment at a target position can be performed while checking a treatment tool led out from the standing wall portion through the observation window.

According to another aspect of the present invention, preferably, the standing wall portion is disposed only on the proximal end side of the opening.

With this aspect, because the positon of the standing wall portion is on the proximal end side of the opening, a space can be formed between the ultrasonic transducer and the standing wall portion. Accordingly, even a proximal end side of the ultrasound transmitting/receiving surface of the ultrasonic transducer can be made to be in close contact with a body cavity wall (tissue), the distance between a treatment tool led out from the opening and the body cavity wall can be reduced, and the treatment tool can be more easily inserted to a target position.

According to another aspect of the present invention, preferably, the ultrasonic transducer has an ultrasound transmitting/receiving surface that is formed in a curved shape in the axial direction of the distal end rigid portion.

The present invention can be appropriately used for a convex-type ultrasonic endoscope in which the ultrasound transmitting/receiving surface of the ultrasonic transducer is formed in a curved shape in the axial direction of the distal end rigid portion.

According to another aspect of the present invention, preferably, the ultrasound transmitting/receiving surface has a vertex that is located at an end portion thereof that is furthest toward the one side in the first direction; and, when a position of the vertex in the first direction is defined as a vertex position and a position of an end portion of an upper edge of the standing wall portion that is furthest toward the other side in the first direction is defined as an other-side wall upper end position, the vertex position is identical to the other-side wall upper end position or is located on the one side in the first direction relative to the other-side wall upper end position.

This aspect defines the positions of the upper edge of the standing wall portion and the ultrasonic transducer when the standing wall portion is provided. By locating the vertex position of the ultrasound transmitting/receiving surface in the first direction to be identical to the other-side wall upper end position or on the one side in the first direction relative to the other-side wall upper end position, a treatment tool led out from the standing wall portion can be made closer to the ultrasonic transducer. Accordingly, treatment with a treatment tool can be performed at a position observed by the ultrasonic observation position.

According to another aspect of the present invention, preferably, the observation window is disposed offset from the treatment-tool erecting base in a second direction that is perpendicular to the first direction.

With this aspect, because the observation window is disposed offset from the treatment-tool erecting base in the second direction, when the treatment-tool erecting base is erected, blocking of the field of view of the observation window by the treatment tool and the treatment-tool erecting base can be prevented.

According to another aspect of the present invention, preferably, the treatment-tool erecting base emerges from the opening forming surface.

With this aspect, by causing the treatment-tool erecting base to emerge from the opening forming surface, the treatment-tool erecting base that emerges from the opening can be observed in the field of view of the observation window.

According to another aspect of the present invention, preferably, the ultrasonic endoscope comprises, at the observation means forming surface, a nozzle that ejects a cleaning liquid toward the observation window and a deflection portion that deflects the cleaning liquid that has passed the observation window toward the opening.

With this aspect, because cleaning of the observation window is performed by ejecting the cleaning liquid from the nozzle at the observation means forming surface and because the deflecting portion for deflecting the cleaning liquid toward the opening is provided, the cleaning liquid that has passed the observation window can be directed toward the opening, and the opening can be cleaned with the cleaning liquid.

According to another aspect of the present invention, preferably, the observation means forming surface has an illumination portion, and both side portions of the opening forming surface have light-guiding recessed wall portions that suppress blocking of illumination light from the illumination portion.

With this aspect, by providing the light-guiding recessed wall portions on both sides of the opening forming surface, nonuniform illumination from the illumination portion and generation of a shadowed region can be prevented, and therefore treatment with a treatment tool can be safely performed.

With the ultrasonic endoscope according to the present invention, because the observation window is disposed on the proximal end side of the opening and the position of the observation window in the first direction is located on the one side in the first direction relative to the one-side opening position of the opening, a blind area where a treatment tool led out from the opening is not within the field of view of the observation window can be reduced. Thus, a treatment tool led out from the opening can be checked through the observation window, and treatment can be reliably performed at a target position.

DESCRIPTION OF THE PREFERRED EMBODIMENTS

Hereafter, an ultrasonic endoscope according to the present invention will be described with reference to the drawings.

Ultrasonic Endoscope

Figure 1:
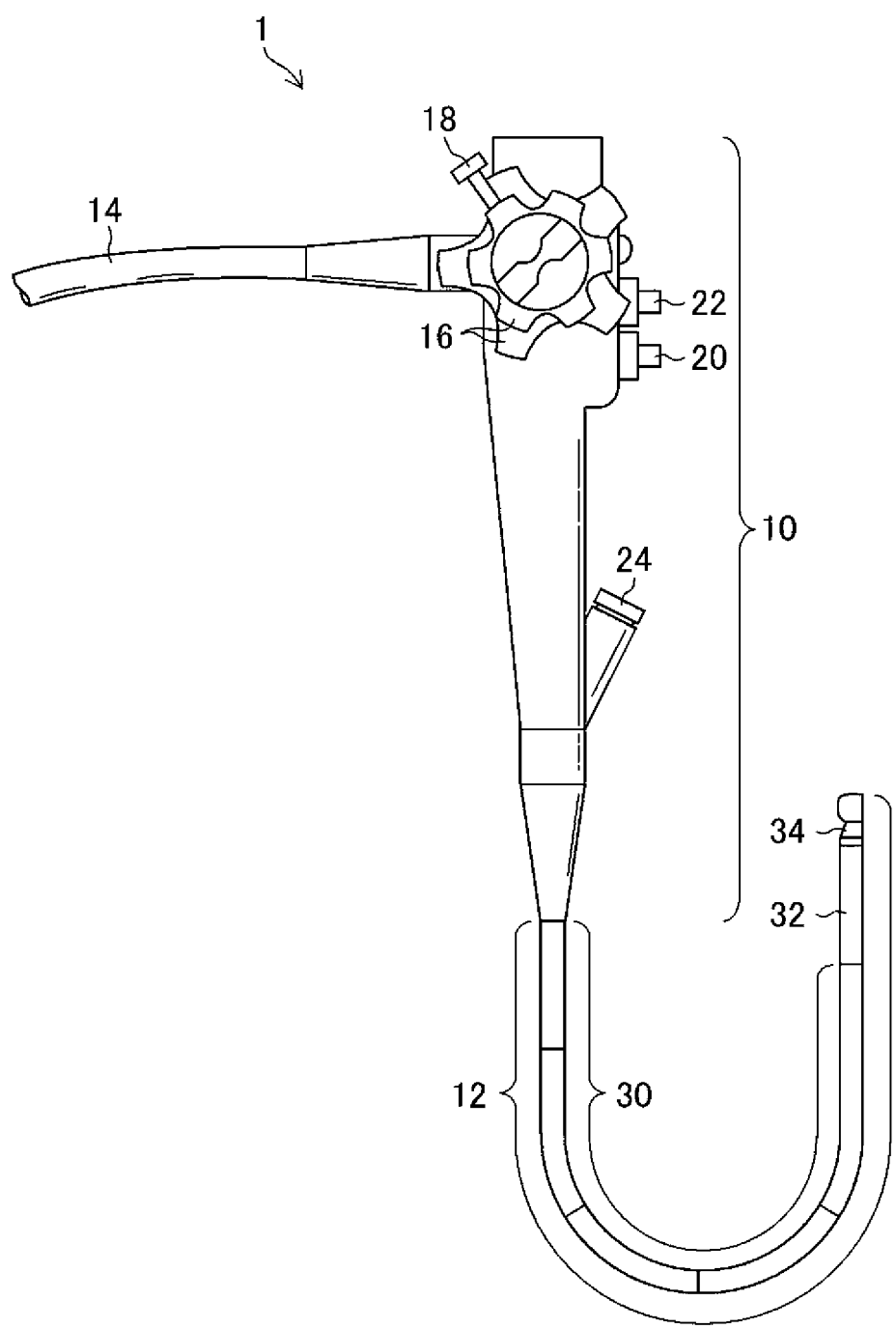
FIG. 1 is an overall view of an ultrasonic endoscope according to the present invention.

FIG. 1 is an overall view of an ultrasonic endoscope 1 to which the present invention is applied.

The ultrasonic endoscope 1 (hereafter, simply referred to as "the endoscope 1") illustrated in the figure includes an operation unit 10 that an operator grips to perform various operations, an insertion section (endoscope insertion section) 12 that is inserted into a body cavity of a patient, and a universal cord 14 for connecting the endoscope 1 to system component devices (not shown) of an endoscope system, such as a processor device and a light source device.

The operation unit 10 has various operation members that are operated by an operator, such as an angle knob 16, whose functions will be described below as necessary, an erecting operation lever 18, an air/water supply button 20, and a suction button 22.

The operation unit 10 has a treatment tool insertion opening 24 from which a treatment tool is inserted into a treatment tool insertion channel, which extends through the insertion section 12.

The insertion section 12 extends from a distal end of the operation unit 10, and has a small-diameter elongated shape as a whole.

The insertion section 12 is composed of a soft portion 30, a bending portion 32, a distal end rigid portion 34, in order from the proximal end side toward the distal end side.

The soft portion 30 occupies most part of the insertion section 12 from the proximal end side, and has flexibility with which the soft portion 30 can be bent in any directions. When the insertion section 12 is inserted into the body cavity, the soft portion 30 is bent along an insertion path into the body cavity.

The bending portion 32 can be bent in the up-down direction and the left-right direction by rotating the angle knob 16 of the operation unit 10. By bending the bending portion 32, the distal end rigid portion 34 can be directed in a desired direction.

As described below in detail, the distal end rigid portion 34 includes an image capturing portion and an illumination portion for capturing an observation image of the inside of a body cavity, an ultrasonic transducer for obtaining an ultrasound image, and a treatment tool lead-out portion for leading out a treatment tool inserted from the treatment tool insertion opening 24. The treatment tool lead-out portion is composed of a treatment tool lead-out port 80, an erecting base housing portion, an erecting base, an opening, an opening forming surface, and the like. In the following description, an erecting base housing portion 62 may be used synonymously with a treatment tool lead-out portion.

The universal cord 14 contains an electric cable, a light guide, and a fluid tube. The universal cord 14 includes a connector at an end portion thereof (not shown). By connecting the connector to predetermined system component devices of the endoscope system, such as a processor device and a light-source device, electric power, control signals, illumination light, liquid, gas, and the like that are necessary to operate the endoscope 1 are supplied from the system component devices to the endoscope; and data of an observation image obtained by the image-capturing portion and data of an ultrasound image obtained by the ultrasonic transducer are transmitted from the endoscope 1 to the system component devices. The observation image and the ultrasound image transmitted to the system component devices are displayed on a monitor, and an operator and the like can observe the images.

Structure of Distal End Rigid Portion

First Embodiment

Figure 2:
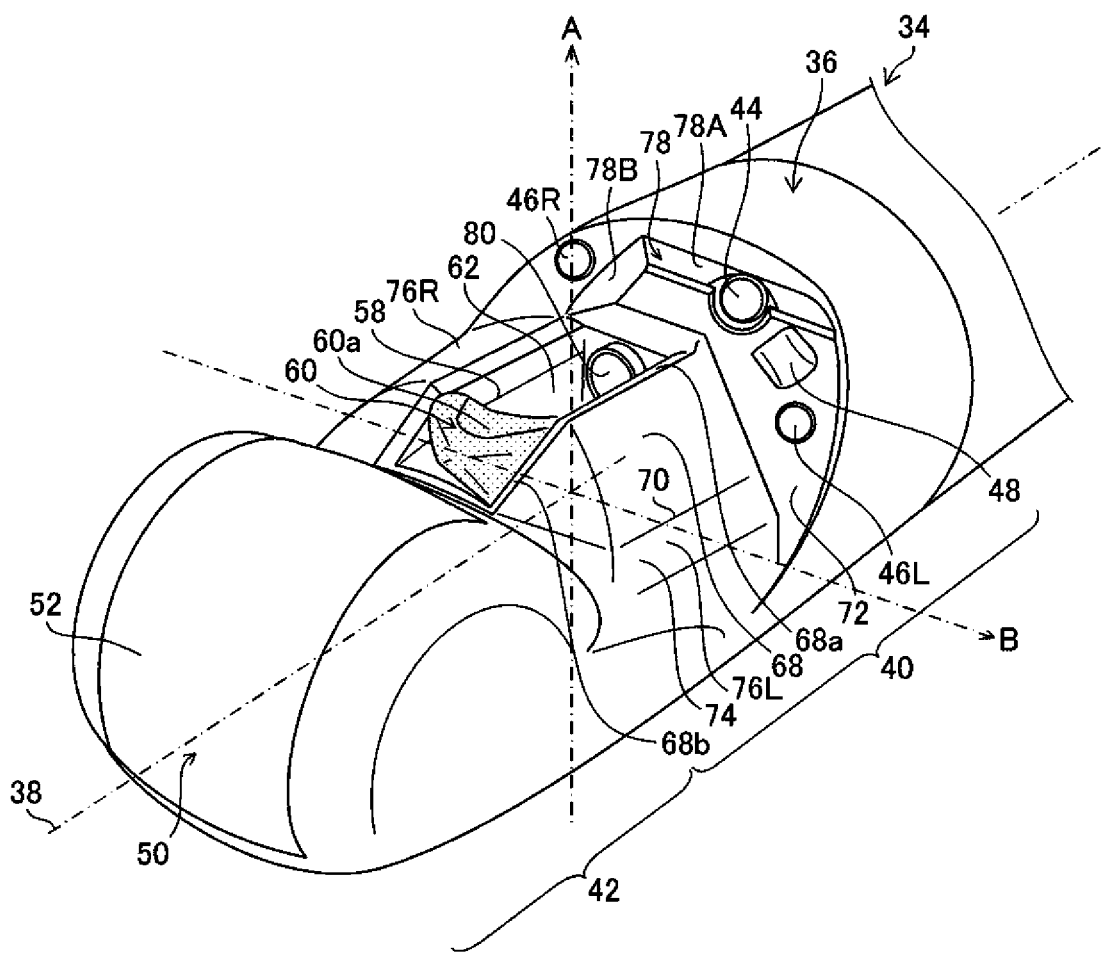
FIG. 2 is an external perspective view of a distal end rigid portion of an insertion section according to a first embodiment.
Figure 3:
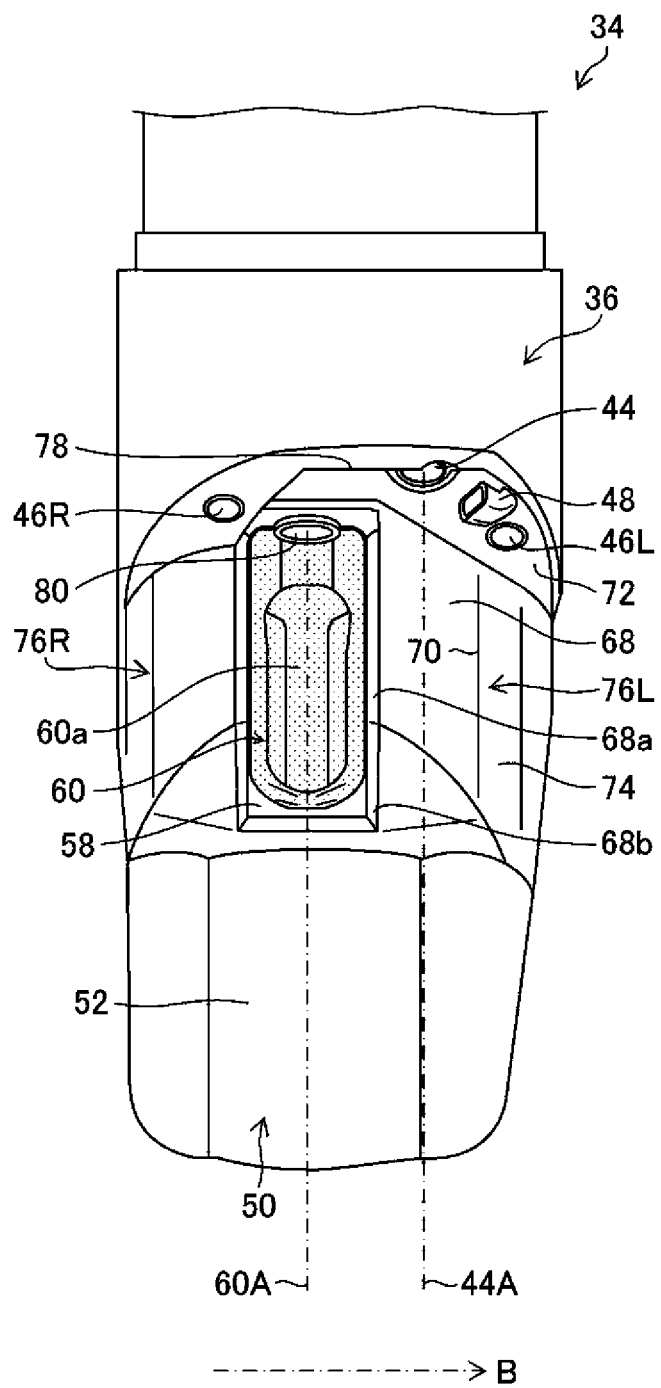
FIG. 3 is an external plan view (top view) of the distal end rigid portion of the insertion section according to the first embodiment.
Figure 4:
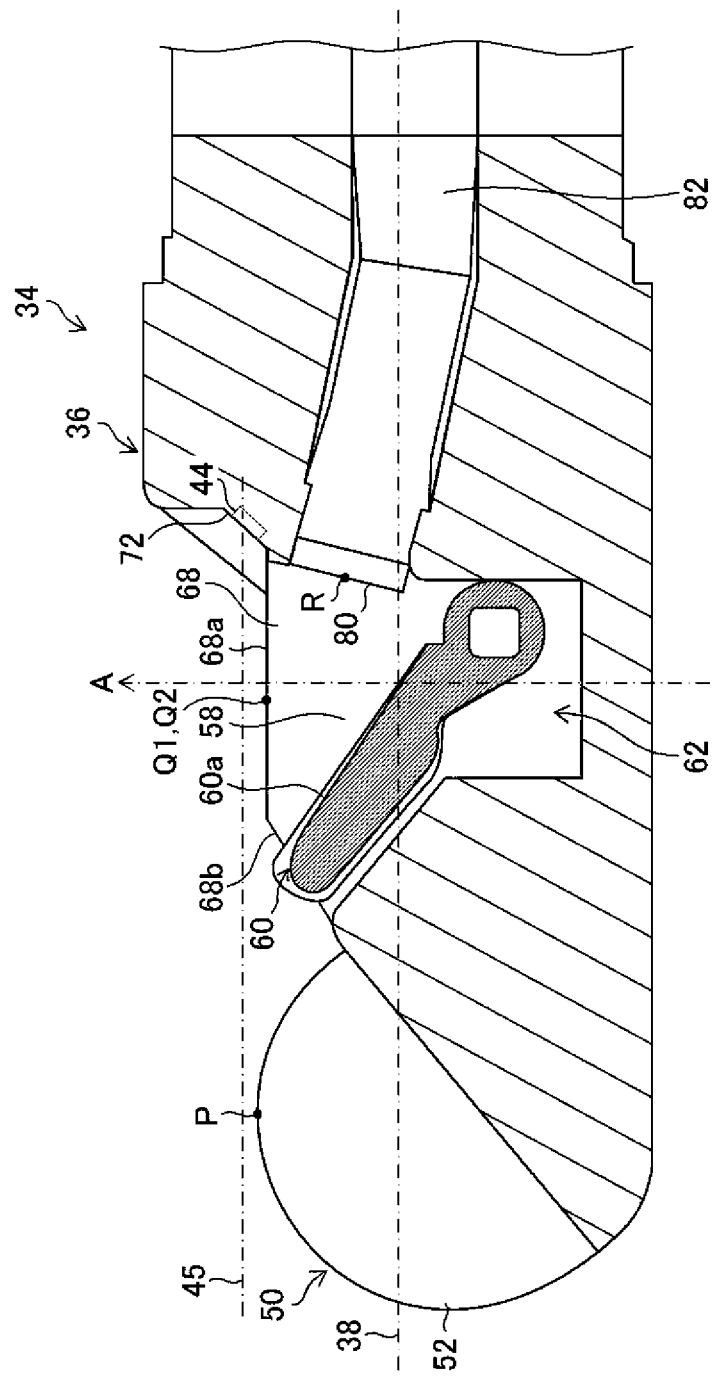
FIG. 4 is a side sectional view of the distal end rigid portion of the insertion section according to the first embodiment.

Next, the structure of the distal end rigid portion 34 of the insertion section 12 will be described. FIG. 2 is an external perspective view of the distal end rigid portion 34, FIG. 3 is a plan view (top view), and FIG. 4 is a side sectional view.

The distal end rigid portion 34 has a distal end rigid portion body (frame body) 36 that forms the outer wall and the inner partition wall thereof. Components disposed in the distal end rigid portion 34 are disposed and held in housing portions (housing chambers) that are defined by the distal end rigid portion body 36.

Although details are omitted, a part of the distal end rigid portion body 36 is removable as a separated block. The components can be installed in a predetermined housing portion in a state in which the separated block is removed. After installing the components in the housing portions, by attaching the separate block to the distal end rigid portion body 36, the components can be disposed and held in the housing portions and fixed to the distal end rigid portion 34.

The distal end rigid portion body 36 is made of an insulating material having insulating properties, which is, for example, a resin material that is a plastic or the like, such as a methacrylate resin or polycarbonate.

As illustrated in FIGS. 2 to 4, the distal end rigid portion 34 is composed of a base member 40 that is included in the distal end rigid portion body 36, and an extension portion 42 that extends from the base member 40 toward the distal end side and holds an ultrasonic transducer 50.

In the extension portion 42, the ultrasonic transducer 50 of a convex-type is disposed. The ultrasonic transducer 50 has, on the upper side thereof, an ultrasound transmitting/receiving surface 52 that is formed by arranging ultrasonic vibrators, for transmitting and receiving ultrasound, in a curved shape in the direction of an axis 38 of the distal end rigid portion 34. The ultrasonic transducer 50 obtains data for generating an ultrasound image of a body tissue. Here, the direction of the axis 38 of the distal end rigid portion 34 is the direction of a line that coincides with or is parallel to the longitudinal axis of the insertion section 12 of FIG. 1. The number of ultrasonic vibrators is not limited and may be one; or two or more ultrasonic vibrators may be disposed.

The base member 40 has an observation window 44, illumination windows 46L and 46R, an air/water supply nozzle 48, an opening 58 for leading out a treatment tool, and a standing wall portion 68 disposed around the opening 58.

The opening 58 is formed at the center of an opening forming surface 70 that is located on the extension portion 42 side of the base member 40. From the opening 58, a treatment tool is led out to an ultrasound scanning range of the ultrasonic transducer 50. The opening 58 is formed in the opening forming surface 70 so that an opening direction thereof is toward one side, in a first direction that is perpendicular to the axis 38 of the distal end rigid portion 34, of the erecting base housing portion 62 of the distal end rigid portion body 36. The opening 58 may be formed so that an opening direction thereof has a component toward the one side in the first direction and a component toward the distal end side in the direction of the axis 38 of the distal end rigid portion 34. That is, the opening may be formed so as to be open upward (toward the one side in the first direction) toward the distal end of the distal end rigid portion 34. Here, the term "opening direction" refers to a direction normal to a surface surrounded by the edge of the opening 58. In the present description, the phrase "one side in the first direction" refers to a direction, as indicated by arrow A in FIG. 4, that is perpendicular to the axis 38 of the distal end rigid portion 34 and in which the opening 58 of the erecting base housing portion 62 is formed. The term "second direction" refers to a direction, as indicated by arrow B in FIG. 2, that is perpendicular to the axis 38 of the distal end rigid portion 34 and to the first direction indicated by arrow A. In the present description, the one side in the first direction may be referred to as "up" and "upward", and the other side in the first direction may be referred to as "down" and "downward".

A treatment tool is inserted from the treatment tool insertion opening 24 of the operation unit 10. The opening forming surface 70 is formed of a surface that has a normal component in the opening direction. In the first embodiment, the opening direction is toward the one side in the first direction, and the opening-forming surface is parallel to the axis 38 of the distal end rigid portion 34. The opening-forming surface may be inclined downward (the other side in the first direction) toward the distal end side of the distal end rigid portion 34. The opening 58 is a portion through which a treatment tool is led out from the erecting base housing portion 62 via an erecting base 60 (described below).

By locating the position of the opening 58 on the proximal end side of the ultrasonic transducer 50 and on the distal end side relative to an observation means forming surface 72 as described below, the distance between the ultrasonic transducer 50 and the opening 58 can be reduced. Accordingly, it is possible to reduce the distance from a position of a treatment tool that has just been led out from the opening 58 to a treatment target position to be treated with the treatment tool. As a result, horizontal displacement of the treatment tool can be reduced, and the treatment tool can be inserted to a target position.

The standing wall portion 68 is formed around the opening 58. With the standing wall portion 68, horizontal displacement of a treatment tool that is led out from the opening 58 can be prevented, and treatment of a target position can be stably performed by using the treatment tool. It is sufficient that the standing wall portion 68 can prevent horizontal displacement of a treatment tool, and it is not necessary that the standing wall portion 68 be formed around the entirety of the opening 58. To be specific, preferably, the standing wall portion 68 is formed so as to stand upward from both sides of the direction in which the treatment tool is led out from the opening 58. In the first embodiment, the standing wall portion 68 stands on the entirety of the opening forming surface 70. The opening forming surface 70 and the standing wall portion 68 may be integrally formed.

The distal end rigid portion body 36 has light-guiding recessed wall portions 76L and 76R, where left-side and right-side portions of an opening-forming surface portion 74 of the opening forming surface 70 are cut off diagonally downward. By forming the light-guiding recessed wall portions 76L and 76R in this way, blocking of illumination light from the illumination windows 46L and 46R is suppressed, and occurrence of nonuniform illumination and generation of a shadowed region can be prevented. The light-guiding recessed wall portions 76L and 76R need not be cut off diagonally downward, and may be cut off in the vertical direction or may be cut off diagonally forward.

The observation window 44 is disposed in the observation means forming surface 72 located on the proximal end side of the opening forming surface 70. Inside of the observation means forming surface 72, an imaging system unit, in which an image-forming optical system and a solid-state imaging element of an imaging unit are integrally assembled, is disposed. Thus, light from a subject in the field of view of the image-capturing portion enters through the observation window 44, a subject image is formed by the image-forming optical system, and the subject image is captured as an observation image by the solid-state imaging element. The observation means forming surface 72 is formed of a surface that has a normal component toward the distal end side in the direction of the axis 38 of the distal end rigid portion 34. In the first embodiment, the observation means forming surface 72 is formed as an inclined surface that is inclined upward toward the proximal end side of the distal end rigid portion body 36. By forming the observation means forming surface 72 as a surface having a normal component toward the distal end side and by forming the observation window 44, a treatment tool that is led out from the opening can be checked through the observation window 44. The observation means forming surface 72 may be formed of a perpendicular surface that is perpendicular to the direction of the axis 38 of the distal end rigid portion 34.

The illumination windows 46L and 46R are formed in the observation means forming surface 72 on both sides of the observation window 44. A light emitting portion of the illumination portion is disposed inside of the observation means forming surface 72. From the light emitting portion, illumination light that is transmitted from the light source device connected to the universal cord 14 through the light guide is emitted. The illumination light illuminates a subject in the field of view of the image-capturing portion through the illumination windows 46L and 46R.

The air/water supply nozzle 48 is formed at the observation means forming surface 72. When the air/water supply button 20 of the operation unit 10 is operated, the air/water supply nozzle 48 ejects a cleaning liquid, water, air, or the like (hereinafter, referred to as "cleaning liquid or the like") toward the observation window 44 to perform cleaning or the like of the observation window 44.

The observation means forming surface 72 has a deflecting portion 78 at a position that is opposite the air/water supply nozzle 48 with the observation window 44 therebetween. The deflecting portion 78 is disposed so as to protrude from the observation means forming surface 72. The deflecting portion 78 may be integrally formed with the observation means forming surface 72 or may be fixed as an independent portion. A cleaning liquid or the like that is ejected from the air/water supply nozzle 48 toward the observation window 44 collides with the deflecting portion 78. The cleaning liquid or the like that has collided with the deflecting portion 78 is deflected toward the opening 58, and is supplied to the opening 58. Thus, cleaning or the like of the inside of the opening 58 is performed.

The shape of the deflecting portion 78 is not particularly limited, as long as the deflecting portion 78 can deflect the cleaning liquid or the like that has passed the observation window 44 toward the opening 58. As illustrated in FIGS. 2 and 3, the deflecting portion 78 may be formed of two surfaces 78A and 78B, which are flat surfaces that are perpendicular to each other. The deflecting portion 78 may be formed of a surface that has a curved shape, such as an arc shape, an elliptical arc shape, or a parabolic shape.

The erecting base housing portion 62, which is disposed continuously with the opening 58, is formed in the opening 58. The treatment tool lead-out port 80 of a treatment tool insertion channel 82 is disposed on the proximal end side of the erecting base housing portion 62.

The treatment tool lead-out port 80 communicates with the treatment tool insertion channel 82 extending through the insertion section 12. A treatment tool inserted from the treatment tool insertion opening 24 of the operation unit 10 (see FIG. 1) is led out from the treatment tool lead-out port 80 to the erecting base housing portion 62.

The erecting base (treatment-tool erecting base) 60 is disposed at a position in the erecting base housing portion 62 in front of the treatment tool lead-out port 80.

The erecting base 60 is made of a metal material such as stainless steel, and has, at an upper side thereof, a guide surface 60a that has a concave shape that is curved upward from the proximal end side toward the distal end side of the distal end rigid portion body 36. A treatment tool led out from the treatment tool lead-out port 80 is bent upward along the guide surface 60a with respect to the direction of the axis 38 of the distal end rigid portion 34 (the longitudinal direction of the insertion section 12) and is led to the outside from the opening 58 on the upper side of the erecting base housing portion 62 and the edge of the standing wall portion 68.

The erecting base 60 can be erected by operating the erecting operation lever 18 of the operation unit 10. The lead-out direction (lead-out angle) of a treatment tool that is led out from the opening 58 can be adjusted by erecting the erecting base 60 and adjusting the erection angle from a prostrate state.

Figure 5:
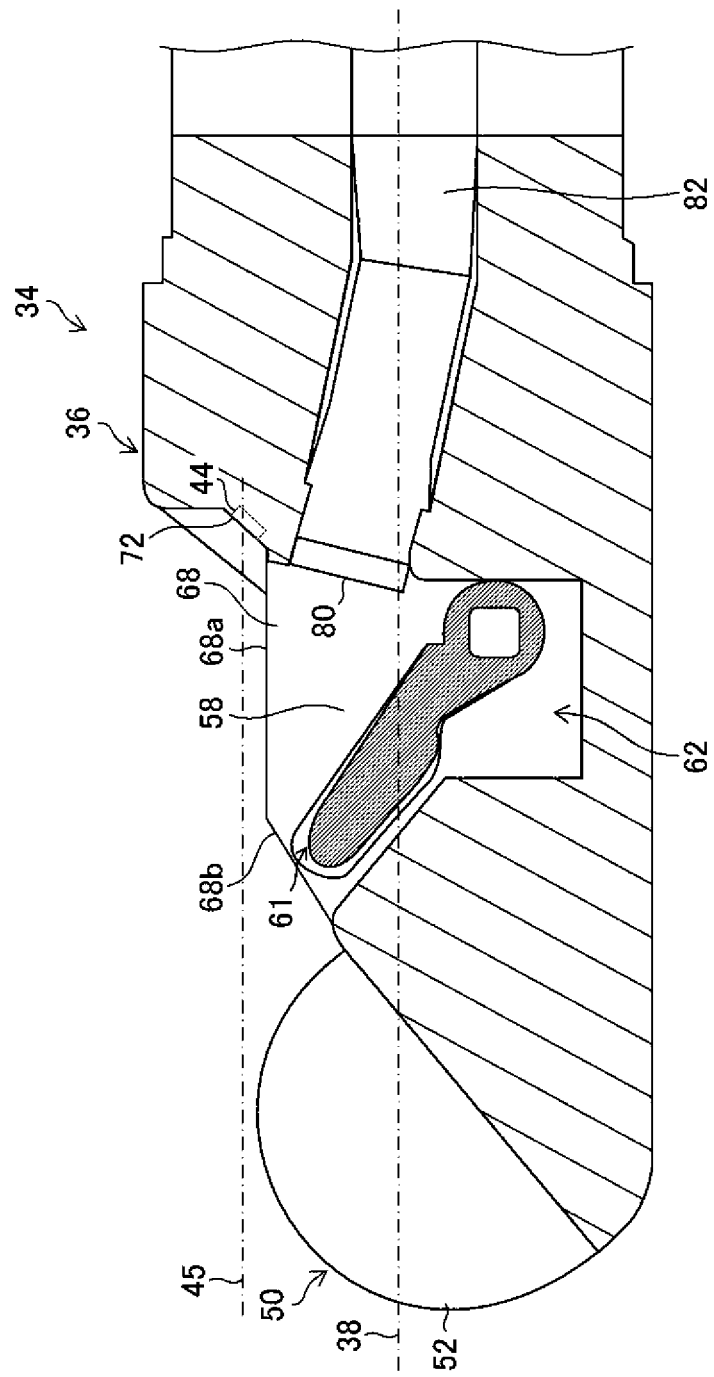
FIG. 5 is a side sectional view of an erecting base of a distal end rigid portion according to a modification.

FIG. 5 is a side sectional view of an erecting base 61 of a distal end rigid portion according to a modification. With the erecting base 60 according to the first embodiment, which is illustrated in FIG. 4, when the erecting base 60 is in a prostrate position (a fully lowered state), a distal end part of the erecting base 60 protrudes from a front edge 68b of the standing wall portion 68. In contrast, when the erecting base 61 illustrated in FIG. 5 is in a fully lowered state, the distal end part of the erecting base 61 does not protrude from the standing wall portion 68, and the entirety of the erecting base 61 is disposed in the erecting base housing portion 62. With a structure such that the erecting base 61 is disposed in the erecting base housing portion 62 in the fully lowered state, the insertion section 12 can be smoothly inserted into a human body.

The treatment tool insertion channel 82 is coupled also to a suction channel (not shown). By operating the suction button 22 of the operation unit 10, suction of a bodily fluid or the like through the opening 58 can be also performed.

Next, the positional relationship among the opening 58 of the distal end rigid portion body 36, an upper edge 68a of the standing wall portion 68, the observation window 44, and the ultrasonic transducer 50 will be described.

In the present embodiment, in the distal end rigid portion body 36, when the position of an end portion of the upper edge 68a of the standing wall portion 68 that is furthest toward the one side in the first direction indicated by arrow A (the up-down direction in FIG. 4) is defined as a one-side wall upper end position Q1, the position of the observation window 44 in the first direction (the up-down direction in FIG. 4) is located on the one side in the first direction relative to the one-side wall upper end position Q1. That is, an axis 45 of the observation window, which extends from the center position of the observation window 44 parallel to the axis 38 of the distal end rigid portion 34, is located above the position of the upper edge 68a. When the standing wall portion 68 is provided, a treatment tool is led to the outside from the upper edge 68a or the front edge 68b of the standing wall portion 68. By locating the upper edge 68a of the standing wall portion 68 below the observation window 44 in this way, a treatment tool led out from the standing wall portion 68 can be reliably placed within the field of view of the observation window 44, the treatment tool can be guided to a target position, and the accuracy of positioning the treatment tool can be improved.

In the first direction of the distal end rigid portion body 36 indicated by arrow A in FIG. 4, the position of the vertex that is located at an end portion of the ultrasound transmitting/receiving surface 52 of the ultrasonic transducer 50 that is furthest toward the one side in the first direction is defined as a vertex position P. The position of an end portion of the upper edge 68a of the standing wall portion 68 that is furthest toward the other side in the first direction is defined as an other-side wall upper end position Q2. Then, in the first direction, the vertex position P is identical to the other-side wall upper end position Q2 or is located on the one side in the first direction relative to the other-side wall upper end position Q2. In FIG. 4, because the upper edge 68a is parallel to the direction of the axis 38 of the distal end rigid portion 34, the one-side wall upper end position Q1 is identical to the other-side wall upper end position Q2. When the upper edge 68a is diagonally formed, the position of the lowest end of the upper edge 68a is defined as the other-side wall upper end position Q2. By disposing the upper edge 68a of the standing wall portion 68 and the ultrasonic transducer 50 so that the vertex position P is identical to the other-side wall upper end position Q2 or is located on the one side in the first direction relative to the other-side wall upper end position Q2, when a treatment tool that has passed through the treatment tool insertion channel 82 is led out diagonally upward from the upper edge 68a or the front edge 68b of the standing wall portion 68, the treatment tool can be led out so as to be close to the ultrasonic transducer 50. Accordingly, the treatment tool can be reliably inserted to a position where ultrasonic observation is performed by using the ultrasonic transducer 50.

When the position of the treatment tool lead-out port 80 in the first direction of the distal end rigid portion body 36 indicated by arrow A in FIG. 4 is defined as a lead-out port position R, the vertex position P is identical to the lead-out port position R or is located on the one side in the first direction relative to (above) the lead-out port position R. A treatment tool passes through the treatment tool insertion channel 82 and is led out diagonally upward from the opening 58, which opens upward. Accordingly, by locating the treatment tool lead-out port 80 below the ultrasonic transducer 50, the treatment tool can be led out to the vicinity of the ultrasonic transducer 50. The lead-out port position R is preferably the center position in the treatment tool lead-out port 80 (see FIG. 4), and more preferably, is filled with the position of an end portion (upper end position) of the treatment tool lead-out port 80 on the one side in the first direction.

As illustrated in FIG. 3, preferably, the observation window 44 is disposed offset from the erecting base 60 in the second direction indicated by arrow B. Here, the clause "the observation window 44 is disposed offset from the erecting base 60 in the second direction" means that, as illustrated in FIG. 3, in a top view, a center line 44A of the observation window 44 is displaced from a center line 60A of the erecting base 60 in the second direction indicated by arrow B. With such a structure, even in a state in which the erecting base 60 is erected and a treatment tool is led out from the standing wall portion 68, blocking of the field of view of the observation window 44 by the treatment tool and the erecting base 60 can be prevented, and a treatment target position can be checked through the observation window 44.

Figure 6:
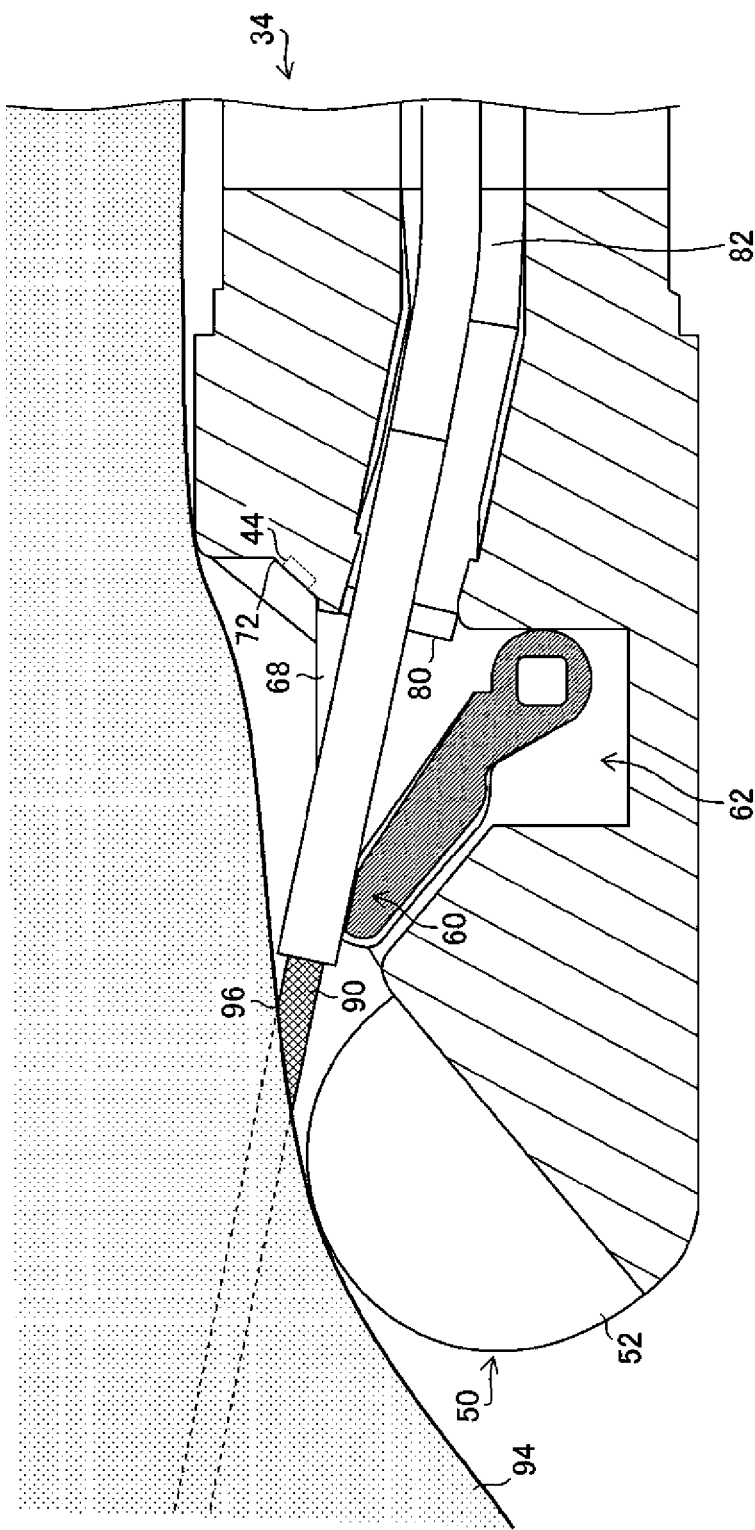
FIG. 6 illustrates a state in which a stent is inserted into a body cavity wall.
Figure 7:
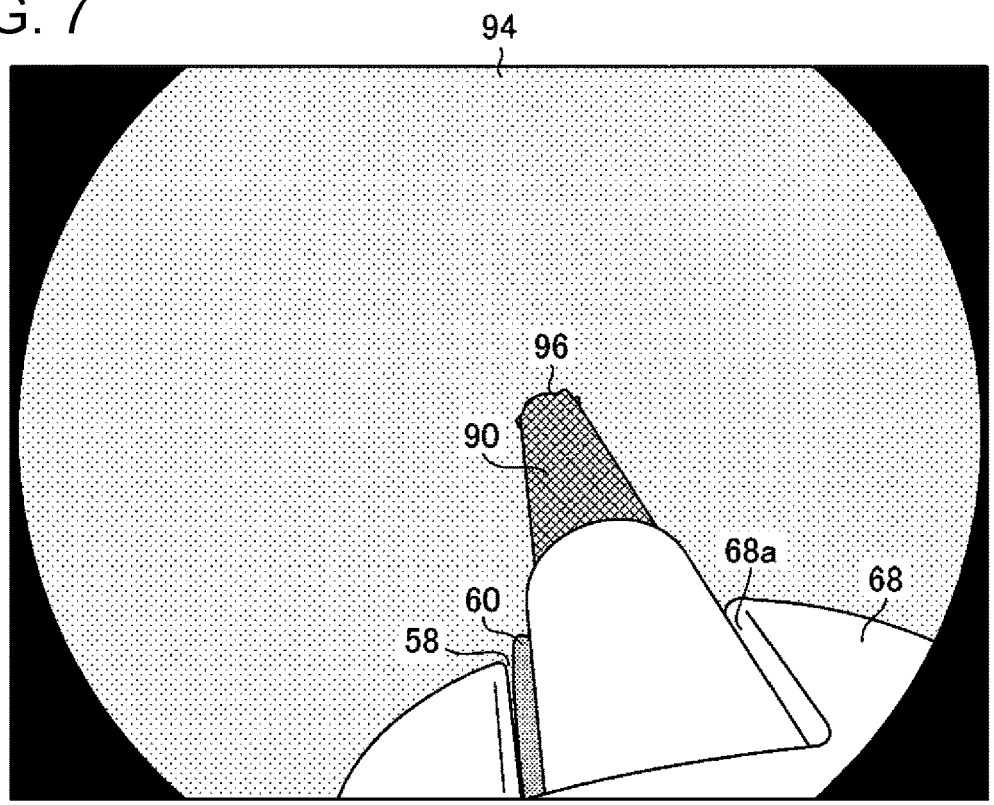
FIG. 7 illustrates an optical image of the inserted state that is captured through an observation window.

Next, as an example of treatment performed by using an ultrasonic endoscope according to the present embodiment, an example of placing a stent will be described. FIG. 6 illustrates a state in which a stent is inserted into a body cavity wall. FIG. 7 illustrates an optical image of the inserted state, which is captured through the observation window.

With the present embodiment, as illustrated in FIGS. 6 and 7, in a state in which a stent 90 is inserted into a body cavity wall 94, an insertion point 96 can be observed with an optical image of the observation window 44. Accordingly, whether the proximal end side of the stent 90 is exposed can be readily checked from the insertion point 96, and, compared with existing technology, a step of changing the field of view of the observation window 44 by moving the insertion section 12 for checking can be reduced. In FIG. 7, the ultrasound transmitting/receiving surface 52 of the ultrasonic transducer 50, which is hidden by the body cavity wall 94, is not shown.

Second Embodiment

Figure 8:
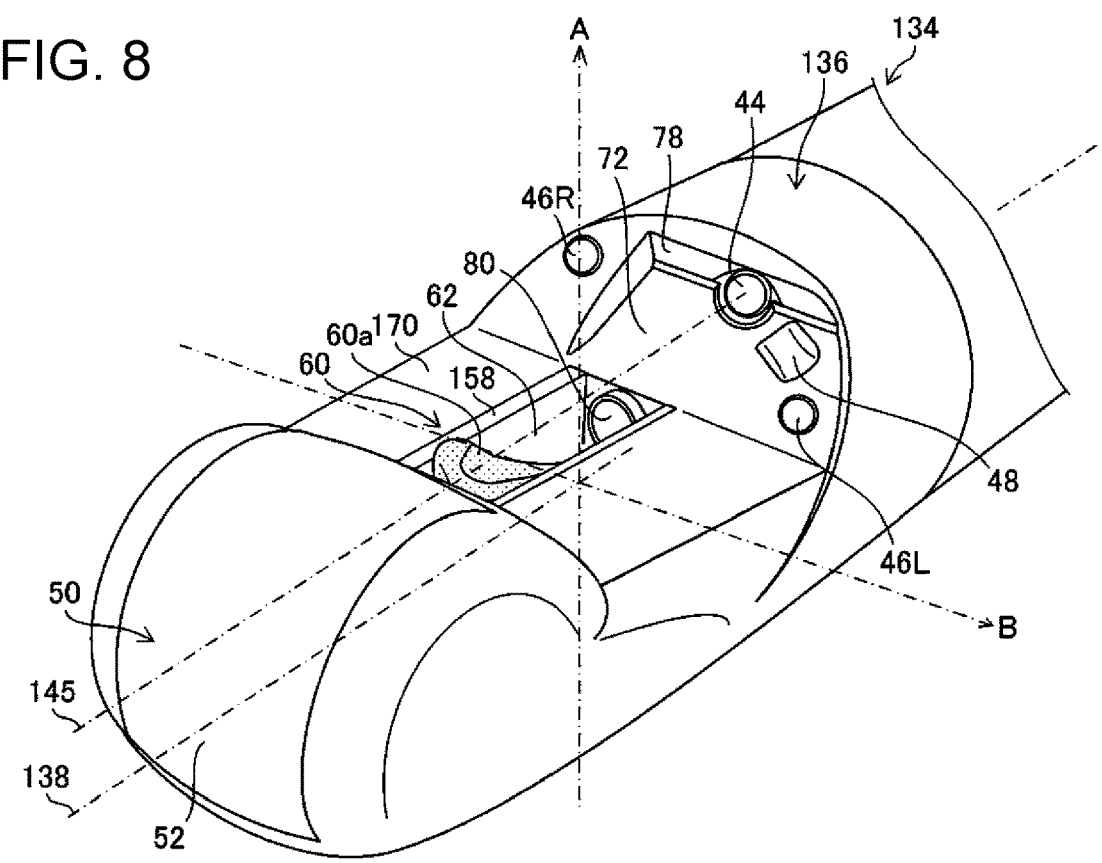
FIG. 8 is an external perspective view of a distal end rigid portion of an insertion section according to a second embodiment.

FIG. 8 is an external perspective view of a distal end rigid portion 134 of an insertion section of an ultrasonic endoscope according to a second embodiment. The distal end rigid portion 134 according to the second embodiment differs from the distal end rigid portion 34 according to the first embodiment in that the distal end rigid portion 134 does not have a standing wall portion and a light-guiding recessed wall portion. In embodiments described below, elements that are the same those of the first embodiment will be denoted by the same numerals and description of such elements may be omitted.

Even without a standing wall portion, in the positional relationship between an opening 158 from which a treatment tool is led to the outside and the observation window 44, by locating the position of the opening 158 on the distal end side relative to the observation window 44 in the distal end rigid portion 134 and locating, in the first direction indicated by arrow A in FIG. 8, a one-side opening position, which is the position of an end portion of the opening that is furthest toward the one-side in the first direction, below an axis 145 of the observation window 44, a treatment tool led out from the opening 158 can be placed within the field of view of the observation window 44. The axis 145 of the observation window 44 is a line extending from the center position of the observation window 44 toward the distal end side, and is a line that is parallel to an axis 138 of the distal end rigid portion 134.

In a case where a treatment tool is led out from the opening 158 to the outside of a distal end rigid portion body 136, preferably, the erecting base 60 emerges from the opening 158. By causing the erecting base 60 to emerge from the opening 158, the erecting base 60 can be checked in the field of view of the observation window 44, and a treatment tool can be led out to a target position by guiding the treatment tool with the erecting base 60.

In the first direction indicated by arrow A in FIG. 8, when the position of an end portion of the opening 158 that is furthest toward the other side in the first direction is defined as an other-side opening position, and the position of a vertex of the ultrasound transmitting/receiving surface 52 of the ultrasonic transducer 50 that is located furthest toward the one side in the first direction is defined as a vertex position, the vertex position is identical to the other-side opening position or is located on the one side in the first direction relative to (above) the other-side opening position.

With such a structure, as with the first embodiment, a treatment tool can be led out so as to be close to the ultrasonic transducer 50.

Modification

Figure 9:
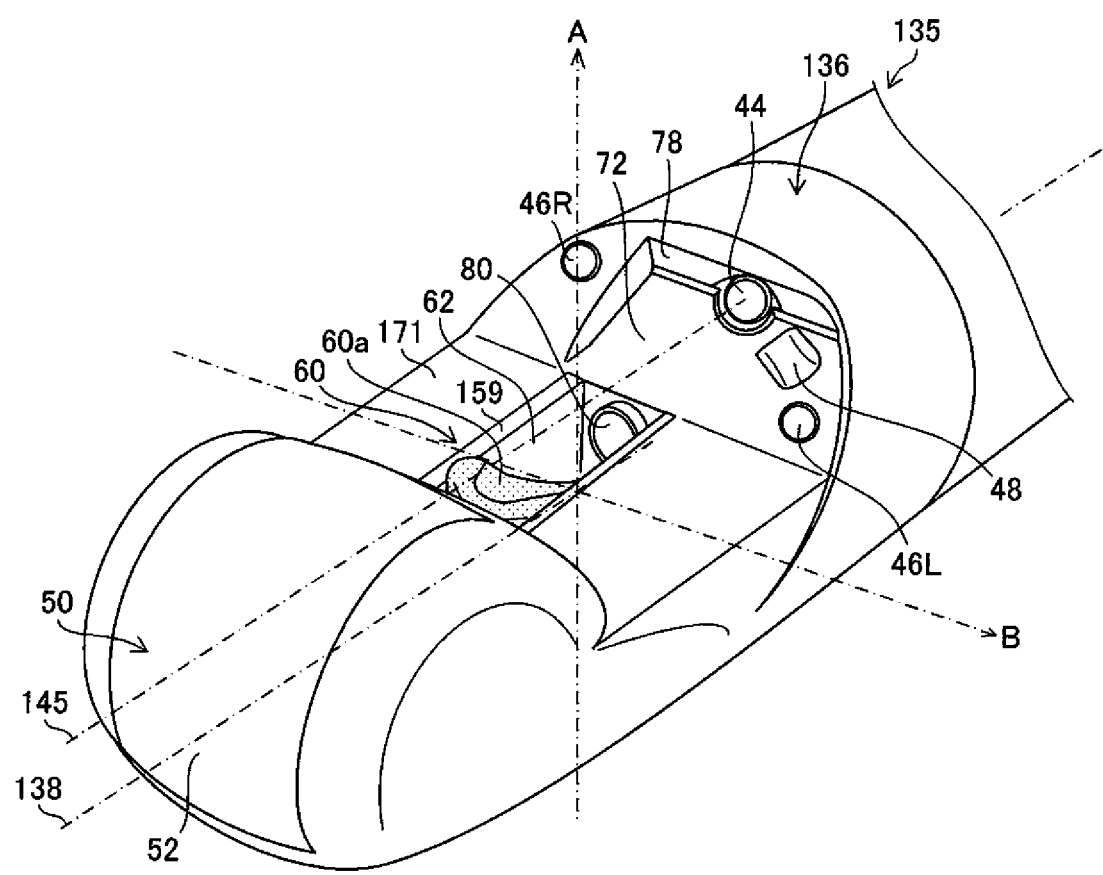
FIG. 9 is an external perspective view of a distal end rigid portion of an insertion section according to a modification of the second embodiment.
Figure 10:
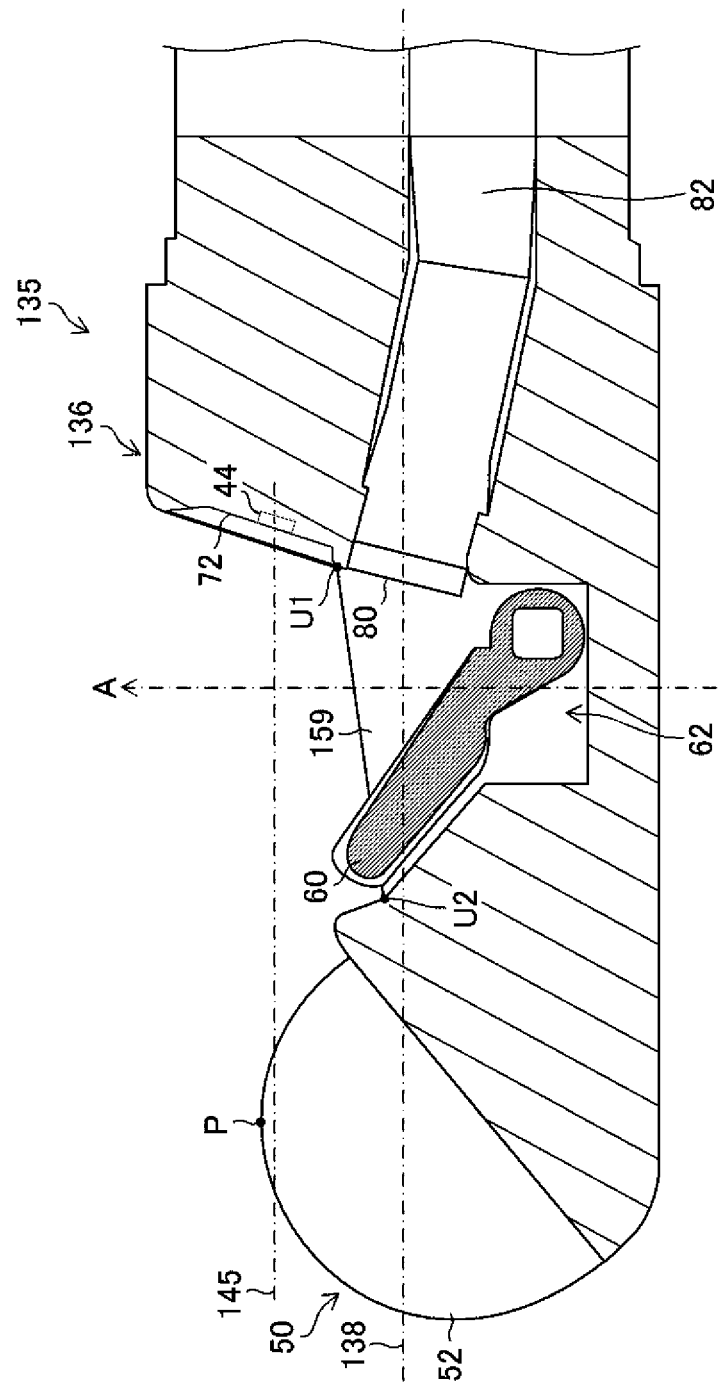
FIG. 10 is a side sectional view of a distal end rigid portion of an insertion section according to a modification of a second embodiment.

FIG. 9 is an external perspective view of a distal end rigid portion 135 of an insertion section of an ultrasonic endoscope according to a modification of the second embodiment, and FIG. 10 is a side sectional view.

The distal end rigid portion 135 illustrated in FIGS. 9 and 10 has an opening 159 whose opening direction has a component toward the one end side in the first direction and a component toward the distal end side in the direction of the axis 138 of the distal end rigid portion 135. The distal end rigid portion 135 differs from the distal end rigid portion 134 illustrated in FIG. 8 in that an opening forming surface 171 is an inclined surface that is inclined toward the one side in the first direction (upward) toward the proximal end side of the distal end rigid portion 135.

Also in the case where the opening forming surface 171 is an inclined surface, in the positional relationship between the opening 159 and the observation window 44, the position of the opening 159 is located on the distal end side of the distal end rigid portion 135 relative to the observation window 44. In the first direction indicated by arrow A in FIG. 10, a one-side opening position U1, which is a position of an end portion of the opening 159 that is furthest toward the one side in the first direction, is located below the axis 145 of the observation window 44. Thus, a treatment tool led out from the opening 159 can be placed within the field of view of the observation window 44.

In the first direction indicated by arrow A in FIG. 10, when the position of an end portion of the opening 159 that is furthest toward the other side in the first direction is defined as an other-side opening position U2, and the position of a vertex of the ultrasound transmitting/receiving surface 52 of the ultrasonic transducer 50 that is located furthest toward the one side in the first direction is defined as a vertex position P, the vertex position P is identical to the other-side opening position U2 or is located on the one side in the first direction relative to (above) the other-side opening position U2. With such a structure, as with the first embodiment, a treatment tool can be led out so as to be close to the ultrasonic transducer 50.

Third Embodiment

Figure 11:
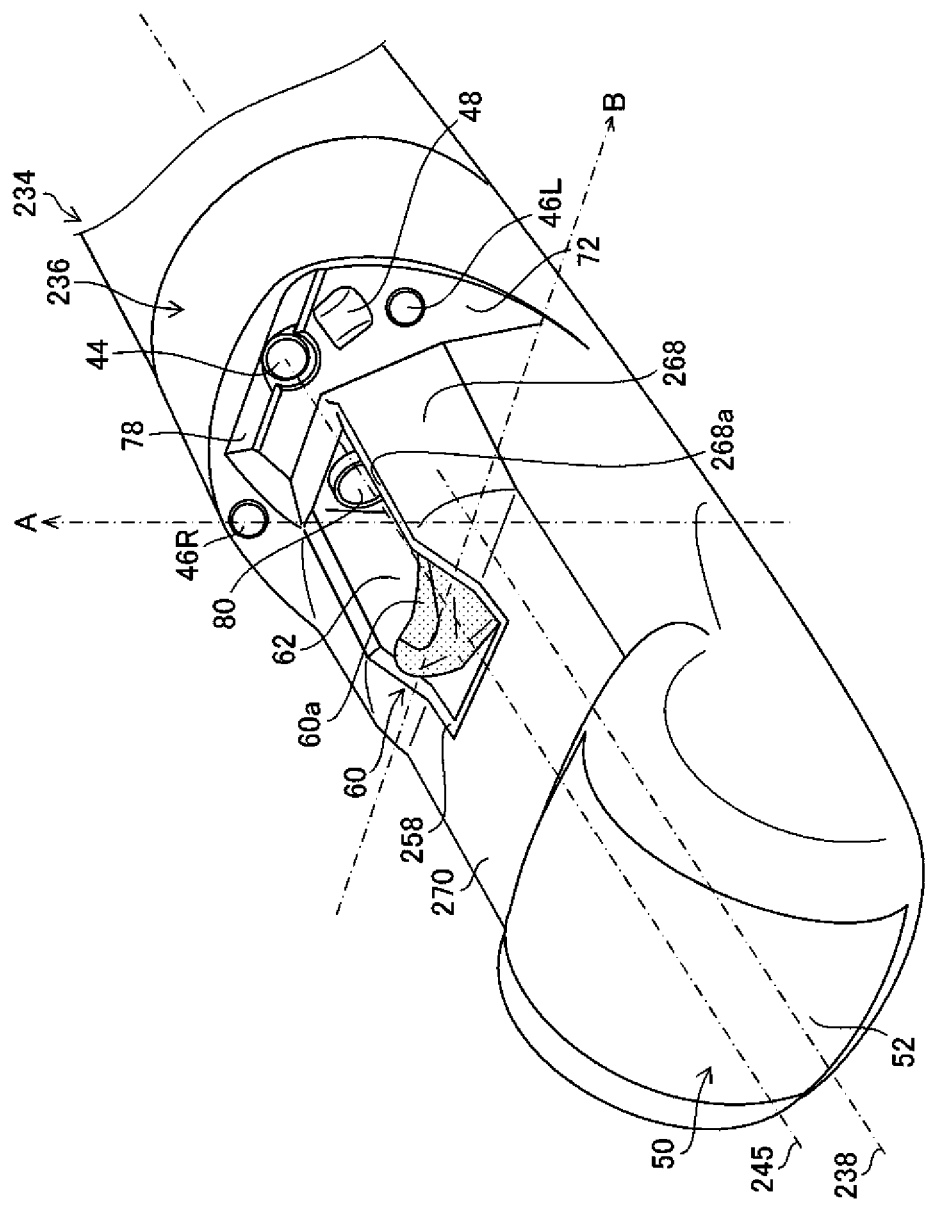
FIG. 11 is an external perspective view of a distal end rigid portion of an insertion section according to a third embodiment.
Figure 12:
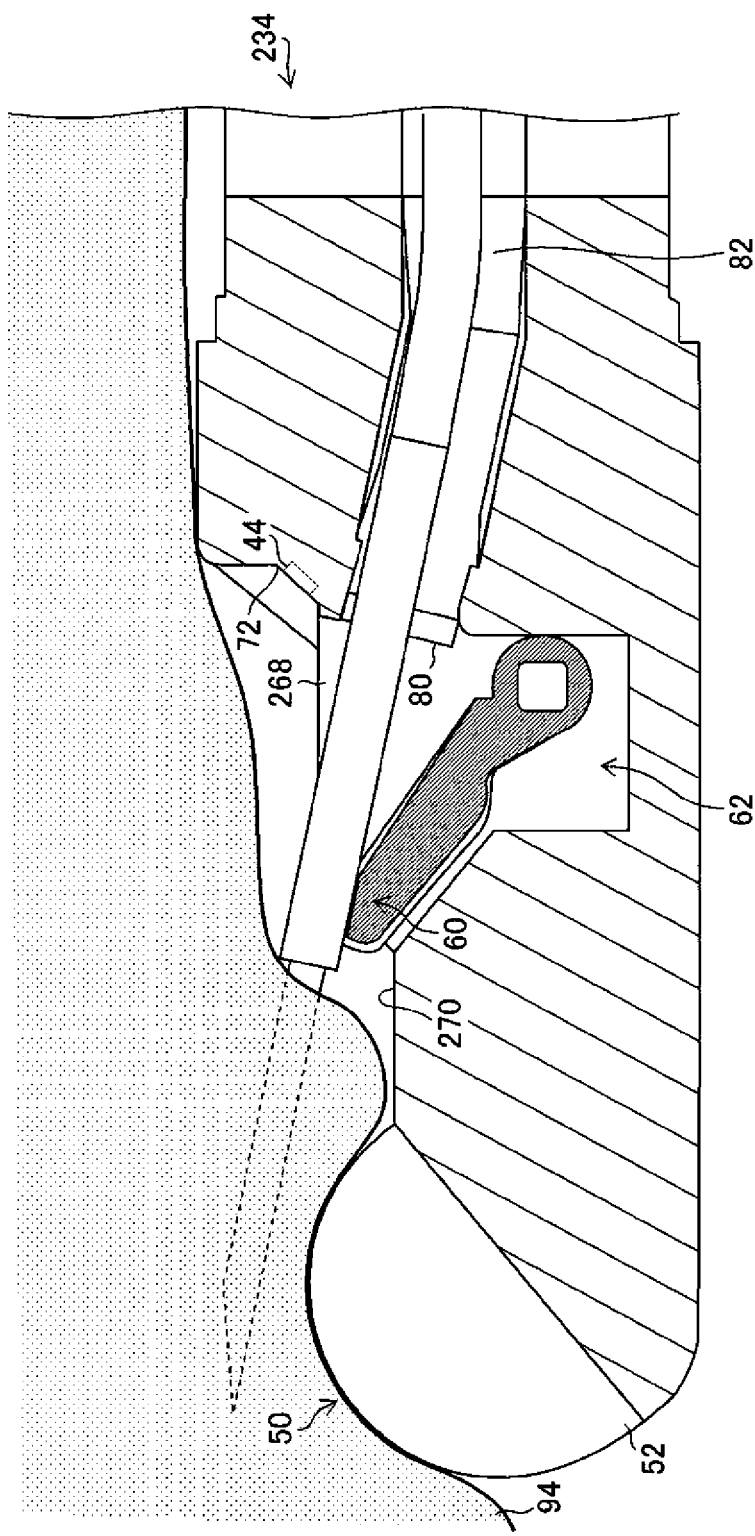
FIG. 12 illustrates a state in which the distal end rigid portion is made to closely contact a body cavity wall.

FIG. 11 is an external perspective view of a distal end rigid portion 234 of an insertion section of an ultrasonic endoscope according to a third embodiment. FIG. 12 illustrates a state in which the distal end rigid portion 234 is made to closely contact the body cavity wall 94.

As illustrated in FIG. 11, the distal end rigid portion 234 of the ultrasonic endoscope according to the third embodiment differs from the distal end rigid portion 34 according to the first embodiment in that the position where a standing wall portion 268 is formed is only on the proximal end side of an opening 258. Even when the standing wall portion 268 is disposed only on the proximal end side of the opening 258, an effect of preventing horizontal displacement can be obtained.

Also with the distal end rigid portion 234 of the ultrasonic endoscope according to the third embodiment, by locating an upper edge 268a of the standing wall portion 268 on the distal end side relative the observation window 44 and by locating, in the first direction indicated by arrow A in FIG. 11, a one-side wall upper end position of the standing wall portion 268 below an axis 245 of the observation window 44, a treatment tool led out from the standing wall portion 268 of a distal end rigid portion body 236 can be placed within the field of view of the observation window 44. The axis 245 of the observation window 44 is a line extending from the center position of the observation window 44 toward the distal end side, and is a line that is parallel to an axis 238 of the distal end rigid portion 234.

As illustrated in FIG. 12, by disposing the standing wall portion 268 only on the proximal end side of the opening 258, the body cavity wall (tissue) 94 can be made to closely contact even the proximal end side of the ultrasound transmitting/receiving surface 52 of the ultrasonic transducer 50. By making the body cavity wall 94 closely contact the ultrasound transmitting/receiving surface 52, the distance between the opening 258 and the body cavity wall 94 can be reduced. Therefore, the position of a treatment tool led out from the opening 258 can be prevented from becoming displaced by a large distance, and treatment can be performed at a target position.

Fourth Embodiment

Figure 13:
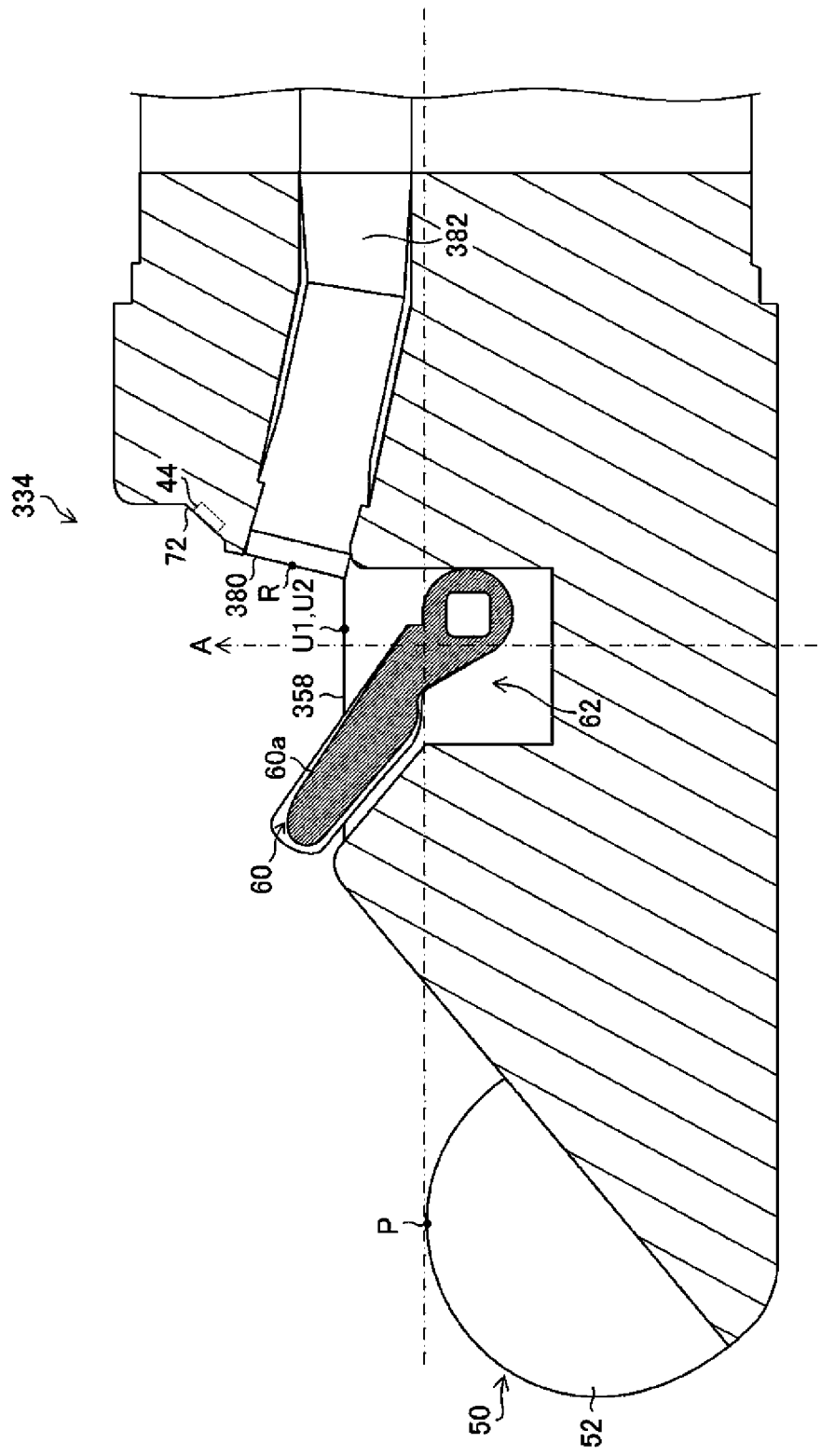
FIG. 13 is a side sectional view of a distal end rigid portion of an insertion section according to a fourth embodiment.

FIG. 13 is a side sectional view of a distal end rigid portion 334 of an ultrasonic endoscope according to a fourth embodiment.

As illustrated in FIG. 13, in the distal end rigid portion 334 of the ultrasonic endoscope according to the fourth embodiment, a one-side opening position U1 of an opening 358 in the first direction indicated by arrow A in FIG. 13 is located on the one side in the first direction relative to (above) the position of a vertex (the vertex position P) of the ultrasound transmitting/receiving surface 52 of the ultrasonic transducer 50 that is located at an end portion that is furthest toward the one side in the first direction. Moreover, a lead-out port position R of a treatment tool lead-out port 380 is located on the one side in the first direction relative to (above) the one-side opening position U1 of the opening 358. Also with the positional relationship illustrated in FIG. 13, by setting the positional relationship between the observation window 44 and the opening 358 so that the opening 358 is on the distal end side relative to the observation window 44 and the one-side opening position U1 is located below the observation window 44, treatment can be performed by using a treatment tool while observing the treatment tool led out from the opening 58 in the field of view of the observation window 44.

Modification

Figure 14:
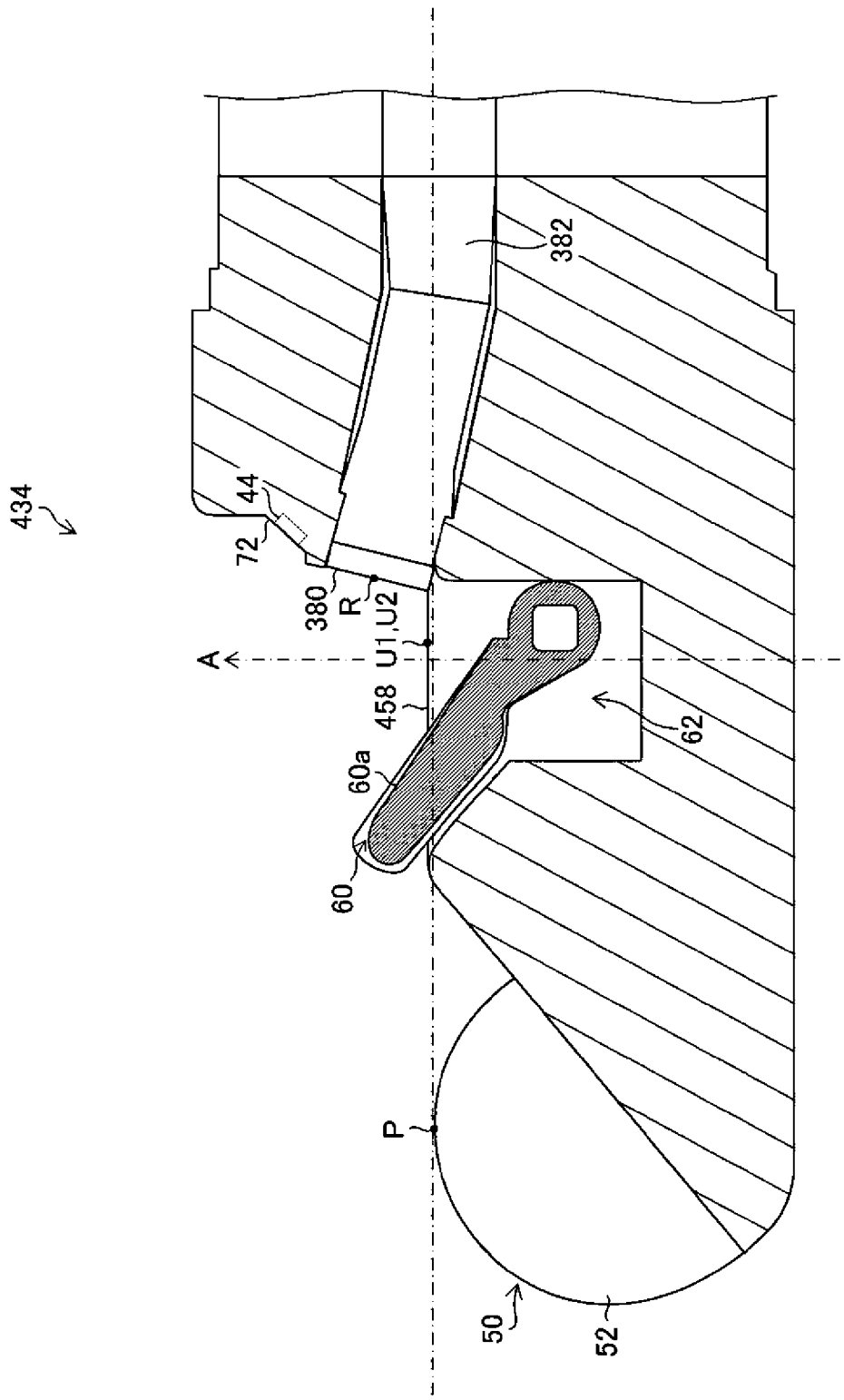
FIG. 14 is a side sectional view of a distal end rigid portion of an insertion section according to a modification of the fourth embodiment.

FIG. 14 is a sectional view of a modification of a distal end rigid portion 434 of an insertion section of an ultrasonic endoscope according to a modification of the fourth embodiment.

The distal end rigid portion 434 illustrated in FIG. 14 differs from the distal end rigid portion 334 illustrated in FIG. 13 in that an other-side opening position U2 of an opening 458 is located at a position identical to the position of a vertex (the vertex position P) of the ultrasound transmitting/receiving surface 52 of the ultrasonic transducer 50 at an end portion that is furthest toward the one side in the first direction indicated by arrow A in FIG. 14. The other-side opening position U2 of the opening 458 may be identical to the vertex position P of the ultrasound transmitting/receiving surface 52 or is located below the vertex position P. By locating the other-side opening position U2 of the opening 458 at a position identical to or below the vertex position P of the ultrasound transmitting/receiving surface 52, the outer size of the distal end rigid portion 434 can be reduced.

REFERENCE SIGNS LIST 1 ultrasonic endoscope
10 operation unit
12 insertion section
14 universal cord
16 angle knob
18 erecting operation lever
20 air/water supply button
22 suction button
24 treatment-tool insertion opening
30 soft portion
32 bending portion
34, 134, 135, 234, 334, 434 distal end rigid portion
36, 136, 236 distal end rigid portion body (frame body)
38, 138, 238 axis of distal end rigid portion
40 base member
42 extension portion
44 observation window
44A center line of observation window
45, 145, 245 axis of observation window
46L, 46R illumination window
48 air/water supply nozzle
50 ultrasonic transducer
52 ultrasound transmitting/receiving surface
58, 158, 159, 258, 358, 458 opening
60, 61 erecting base (treatment-tool erecting base)
60A center line of erecting base
60a guide surface
62 erecting base housing portion
68, 268 standing wall portion
68a, 268a upper edge
68b front edge
70, 171 opening forming surface
72 observation means forming surface
74 opening-forming surface portion
76L, 76R light-guiding recessed wall portion
78, 78A, 78B deflecting portion
80, 380 treatment tool lead-out port
82 treatment tool insertion channel
90 stent
94 body cavity wall (tissue)
96 insertion point

What is claimed is:

1. An ultrasonic endoscope comprising:
a distal end rigid portion that is located at a distal end of an endoscope insertion section;
an ultrasonic transducer that is disposed in the distal end rigid portion;
a treatment tool lead-out portion that is disposed on a proximal end side of the ultrasonic transducer and that comprises
an erecting base housing portion that has an opening whose opening direction is toward one side in a first direction that is perpendicular to an axial direction of the distal end rigid portion or whose opening direction is a direction that has a component toward the one side in the first direction and a component toward a distal end side in the axial direction of the distal end rigid portion,
an opening forming surface in which the opening is formed and that has a normal component in the opening direction,
a treatment tool lead-out port that communicates with an inside of the erecting base housing portion and from which a treatment tool is led out, and
a treatment-tool erecting base that is disposed in the inside of the erecting base housing portion and that changes a lead-out direction of the treatment tool led out from the treatment tool lead-out port; and
an observation window that is disposed on a proximal end side of the opening forming surface and that is disposed in an observation means forming surface that has a normal component toward the distal end side in the axial direction of the distal end rigid portion,
wherein, when a position of an end portion of the opening that is furthest toward the one side in the first direction is defined as a one-side opening position, a position of the observation window in the first direction is located on the one side in the first direction relative to the one-side opening position, and
wherein the observation window is disposed offset from the treatment-tool erecting base in a second direction that is perpendicular to the axial direction of the distal end rigid portion and perpendicular to the first direction.

2. The ultrasonic endoscope according to claim 1, wherein the ultrasonic transducer has an ultrasound transmitting/receiving surface that is formed in a curved shape in the axial direction of the distal end rigid portion.

3. The ultrasonic endoscope according to claim 2, wherein:
the ultrasound transmitting/receiving surface has a vertex that is located at an end portion thereof that is furthest toward the one side in the first direction, and
a position of the vertex in the first direction is defined as a vertex position;
the opening direction is toward the one side in the first direction; and
the vertex position is identical to the one-side opening position in the first direction or is located on the one side in the first direction relative to the one-side opening position.

4. The ultrasonic endoscope according to claim 3, wherein, when a position of the treatment tool lead-out port in the first direction is defined as a lead-out port position, the vertex position is identical to the lead-out port position in the first direction or is located on the one side in the first direction relative to the lead-out port position.

5. The ultrasonic endoscope according to claim 2, wherein:
the ultrasound transmitting/receiving surface has a vertex that is located at an end portion thereof that is furthest toward the one side in the first direction, and a position of the vertex in the first direction is defined as a vertex position;
the opening direction is the direction that has the component toward the one side in the first direction and the component toward the distal end side in the axial direction of the distal end rigid portion;
the opening has an edge that is located on the opening forming surface, the edge of the opening has an uppermost position and a lowermost position in the first direction, the uppermost position of the edge is identical to the one-side opening position, and the lowermost position of the edge is a position that is furthest toward a side opposite to the one side in the first direction; and
the vertex position is identical to the lowermost position of the edge in the first direction or is located on the one side in the first direction relative to the lowermost position of the edge.

6. The ultrasonic endoscope according to claim 5, wherein, when a position of the treatment tool lead-out port in the first direction is defined as a lead-out port position, the vertex position is identical to the lead-out port position in the first direction or is located on the one side in the first direction relative to the lead-out port position.

7. The ultrasonic endoscope according to claim 1, wherein the ultrasonic endoscope has a standing wall portion around the opening, the standing wall portion standing from the opening, and
wherein, when a position of an end portion of an upper edge of the standing wall portion that is furthest toward the one side in the first direction is defined as a one-side wall upper end position, the position of the observation window in the first direction is located on the one side in the first direction relative to the one-side wall upper end position.

8. The ultrasonic endoscope according to claim 7, wherein the standing wall portion is disposed only on the proximal end side of the opening.

9. The ultrasonic endoscope according to claim 8, wherein the ultrasonic transducer has an ultrasound transmitting/receiving surface that is formed in a curved shape in the axial direction of the distal end rigid portion.

10. The ultrasonic endoscope according to claim 9, wherein:
the ultrasound transmitting/receiving surface has a vertex that is located at an end portion thereof that is furthest toward the one side in the first direction, and
a position of the vertex in the first direction is defined as a vertex position;
the upper edge is parallel to the axial direction of the distal end rigid portion; and
the vertex position is identical to the one-side wall upper end position in the first direction or is located on the one side in the first direction relative to the one-side wall upper end position.

11. The ultrasonic endoscope according to claim 9, wherein:
the ultrasound transmitting/receiving surface has a vertex that is located at an end portion thereof that is furthest toward the one side in the first direction, and a position of the vertex in the first direction is defined as a vertex position;
the upper edge is formed diagonally with respect to the axial direction of the distal end rigid portion;
the upper edge has an uppermost position and a lowermost position in the first direction, the uppermost position of the upper edge is identical to the one-side wall upper end position, and the lowermost position of the upper edge is a position that is furthest toward a side opposite to the one side in the first direction; and
the vertex position is identical to the lowermost position of the upper edge in the first direction or is located on the one side in the first direction relative to the lowermost position of the upper edge.

12. The ultrasonic endoscope according to claim 7, wherein the ultrasonic transducer has an ultrasound transmitting/receiving surface that is formed in a curved shape in the axial direction of the distal end rigid portion.

13. The ultrasonic endoscope according to claim 12, wherein:
the ultrasound transmitting/receiving surface has a vertex that is located at an end portion thereof that is furthest toward the one side in the first direction, and
a position of the vertex in the first direction is defined as a vertex position;
the upper edge is parallel to the axial direction of the distal end rigid portion; and
the vertex position is identical to the one-side wall upper end position in the first direction or is located on the one side in the first direction relative to the one-side wall upper end position.

14. The ultrasonic endoscope according to claim 12, wherein:
the ultrasound transmitting/receiving surface has a vertex that is located at an end portion thereof that is furthest toward the one side in the first direction, and a position of the vertex in the first direction is defined as a vertex position;
the upper edge is formed diagonally with respect to the axial direction of the distal end rigid portion;
the upper edge has an uppermost position and a lowermost position in the first direction, the uppermost position of the upper edge is identical to the one-side wall upper end position, and the lowermost position of the upper edge is a position that is furthest toward a side opposite to the one side in the first direction; and
the vertex position is identical to the lowermost position of the upper edge in the first direction or is located on the one side in the first direction relative to the lowermost position of the upper edge.

15. The ultrasonic endoscope according to claim 1, wherein the treatment-tool erecting base emerges from the opening forming surface.

16. The ultrasonic endoscope according to claim 1, wherein the ultrasonic endoscope comprises, at the observation means forming surface, a nozzle that ejects a cleaning liquid toward the observation window and a deflection portion that deflects the cleaning liquid that has passed the observation window toward the opening.

17. The ultrasonic endoscope according to claim 1,
wherein the observation means forming surface has an illumination portion, and
wherein the opening forming surface has two side portions and both side portions of the opening forming surface have light-guiding recessed wall portions that suppress blocking of illumination light from the illumination portion, the both side portions are in a second direction that is perpendicular to the axial direction of the distal end rigid portion and perpendicular to the first direction.

* * * * *